US005668000A

United States Patent [19]
Akiyoshi et al.

[11] Patent Number: 5,668,000
[45] Date of Patent: Sep. 16, 1997

[54] MITOCHONDRIAL P450

[75] Inventors: Megumi Akiyoshi; Yoshiyasu Yabusaki, both of Hyogo; Toshiyuki Sakaki, Osaka; Hideo Ohkawa, Hyogo, all of Japan

[73] Assignee: Sumitomo Chemical Company, Limited, Osaka, Japan

[21] Appl. No.: 702,795

[22] Filed: Aug. 26, 1996

Related U.S. Application Data

[63] Continuation of Ser. No. 420,799, Apr. 12, 1995, abandoned, which is a continuation of Ser. No. 97,922, Jul. 28, 1993, abandoned, which is a continuation of Ser. No. 765,941, Sep. 26, 1991, abandoned.

[30] Foreign Application Priority Data

Sep. 26, 1990 [JP] Japan ................... 2-258262
May 24, 1991 [JP] Japan ................... 3-120123

[51] Int. Cl.⁶ ................... C12N 9/02; C12N 15/81; C12N 1/19; C12N 15/00
[52] U.S. Cl. ................... 435/189; 435/251.21; 435/320.1; 435/69.1
[58] Field of Search ................... 435/69.1, 71.1, 435/172.3, 189, 254.21, 320.1; 536/23.2

[56] References Cited

U.S. PATENT DOCUMENTS 4,766,068  8/1988  Oeda et al. ................... 435/69.1

FOREIGN PATENT DOCUMENTS

| 62-104582 | 5/1987 | Japan . | |
|---|---|---|---|
| 63-112986 | 5/1988 | Japan | C12N 15/00 |
| 64-47380 | 2/1989 | Japan . | |
| 64-63383 | 3/1989 | Japan . | |
| 3-232493 | 10/1991 | Japan . | |
| 89/10963 | 11/1989 | WIPO | C12N 15/00 |

OTHER PUBLICATIONS

Hurt et al., "The Cleavable Prepiece of COXIV carries all the information for Importing an Attached Cytosolic Protein into the Yeast Mitochondrial Matrix," In: Protein Transport and Secretion, Gething, M.J. (ed.) CSHL, Cold Spring Harbor, NY. (1984).
Suet al., "A cDNA encoding a Rat Mitochondrial Cytochrome P450 Catalyzing Both the 26-Hydroxylation of Cholesterol and 25-Hydroxylation of Vitamin $D_3$: Gonadotropic Regulation of the Cognate mRNA in Ovaries,"DNA and Cell Biology 9(9):657–665. (Sep. 1990).
Bjorkhem et al. "Properties of a Reconstituted Vitamin $D_3$25–Hydroxylase from Rat Liver Mitochondria," JBC 255(11):5244–49. (1980).
Zuber et al., "Simultaneous transfection of COS–1 cells with mitochondrial and microsomal steroid hydroxylases:Incorporation of a steroidogenic pathway into nonsteroidogenic Celk," PNAS, 85:699–703 (Feb. 1988).
Kingsman et al., "Heterologous Gene Expression in *Saccharomyces Cerevisiae*," Biotechnology and Bioengineering Reviews, 3:377–415 (1985).
Barnes et al., Proc. Natl. Acad. Sci. USA 88, 5597–5601 (1991).
Zuber et al., Science, 234, 1258–1261 (1986).
Usui et al., Febs Letters, 262(1) 135–138 (1990).
Usui et al., Febs Letters, 274(1,2) 175–177 (1990).
Oeda et al., DNA 4, 203–210 (1985).
Sakaki et al., DNA 8, 409–418 (1989).
Shibata et al., DNA Cell Biol. 9, 27–36 (1990).
Akiyoshi–Shibata et al., Febs Letters 280, 367–370 (1991).
Chemical Abstracts 113:2514w.
Chemical Abstracts 108:218092b.
Okuda et al., J. Biol. Chem., 263, 18138–18142 (1988).
Masumoto et al., J. Biol. Chem., 263, 14256–14260 (1988).
Patent Abstracts Of Japan, vol. 12, No. 110 (C486) (2957) Apr. 8, 1988, JP 62–236495.
Emiko Usui, et al., Molecular cloning of cDNA for vitamin $D_3$25–hydroxylase from rat liver mitochondria, FEBS, Mar. 1990, vol. 262(1), pp. 135–138.
*Biochemical Dictionary;* p. 41, c. 1994 by Tokyo Kagaku Dojinkai.

*Primary Examiner*—Nancy T. Vogel
*Attorney, Agent, or Firm*—Birch, Stewart, Kolasch & Birch, LLP

[57] ABSTRACT

The expression of mitochondrial P450 in yeast is disclosed. The mitochondrial P450 includes a chimeric P450 in which a signal sequence present at the N-terminus of a mammalian mitochondrial P450 has been substituted by a signal of a yeast mitochondrial protein and a chimeric P450 in which the latter signal has been further substituted by a targeting signal sequence to microsome.

An expression plasmid for producing the enzyme in a large scale, a recombinant yeast strain carrying the expression plasmid, a process for producing the enzyme by the use of the recombinant yeast, and a process for producing 5β-cholestane-3α, 7α, 12α, 27-tetrol, 25-hydroxyvitamin $D_3$ and 1α,25-dihydroxyvitamin $D_3$ are also disclosed.

14 Claims, 6 Drawing Sheets

FIG. 5 pAMS25

FIG. 6

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:1:

AATTCAAGCT TAAAAAAATG GCTCTGTTGA GCCGCATGAG A       41

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:2:

CTGAGATGGG CGCTTCTGGA CACTCGTGTG ATGGGC       36

( 2 ) INFORMATION FOR SEQ ID NO:3:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:3:

AGCTTAAAAA AATGCTTTCA CTACGTCAAT CGATAAGATT TTTCAAGCCA GCCACAAGAA C       61

( 2 ) INFORMATION FOR SEQ ID NO:4:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO:4:

TTTGTGTAGC TCTAGATATC TGCTTCAGCA AAAACCCGCG ATCCCTGCA       49

( 2 ) INFORMATION FOR SEQ ID NO:5:

( i ) SEQUENCE CHARACTERISTICS:
( A ) LENGTH: 74 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:5:

```
AATTCAAGCT TAAAAAAATG TGGCTGCTCC TGGCTGTCTT TCTGCTCACC CTCGCCTATT    60
TAGCGATCCC TGCA                                                      74
```

MITOCHONDRIAL P450

This application is a continuation, of application Ser. No. 08/420,799 filed on Apr. 12, 1995, now abandoned; which was a continuation of application Ser. No. 08/097,922 filed on Jul. 28, 1993, now abandoned; which was a continuation of application Ser. No. 07/765,941 filed on Sep. 26, 1991, now abandoned.

BACKGROUND OF THE INVENTION

The present invention relates to the expression of mitochondrial P450 in yeast. The mitochondrial P450 includes a chimeric P450 in which a signal sequence present at the N-terminus of a mammalian mitochondrial P450 has been substituted by a signal of a yeast mitochondrial protein and a chimeric P450 in which the latter signal has been further substituted by a targeting signal sequence to microsome. More specifically, the present invention relates to genes which encode a rat liver mitochondria $P450_{c25}$ precursor, a chimeric P450 in which a matured $P450_{c25}$ is connected with 29 amino acid residues which is believed to be the mitochondrial targeting signal of the yeast cytochrome c oxidase subunit IV (COXIV), and a chimeric P450 in which a signal sequence comprising 15 amino acid residues at the N-terminus of bovine adrenal $P450_{17}\alpha$ which is believed to be the microsomal targeting signal is followed by a matured $P450_{c25}$, respectively.

The present invention further relates to an expression plasmid for producing the enzyme in a large scale, a recombinant yeast strain carrying the expression plasmid, a process for producing the enzyme by the use of the recombinant yeast, and a process for producing 5β-cholestane-3α,7α,12α,27-tetrol (referred to hereinafter as TeHC), 25-hydroxyvitamin $D_3$ and 1α,25-dihydroxyvitamin $D_3$.

The term chimeric P450 used in this specification means hereinafter P450 comprising a foreign N-terminal targeting signal sequence and a matured mitochondrial P450 at C-terminus.

P450 is a hemoprotein existing widely in biological fields from microorganisms to mammals and catalyzes as a terminal enzyme of electron transport chains monooxygenation toward a variety of lipophilic compounds as substrates.

P450 as the terminal enzyme in electron transport chains has a variety of molecular forms, which exhibit different substrate specificities and thus can catalyze the hydroxylation of a wide variety of lipophilic compounds. P450-dependent electrontransport chains in mammals are classified into two groups; microsomal and mitochondrial types.

In microsomes, NADPH-cytochrome P450 reductase (reductase) containing flavin adenine dinucleotide and flavin mononucleotide as cofactors in the molecule transfers electrons from NADPH to P450. In mitochondria, NADPH-ferredoxin reductase containing flavin adenine dinucleotide as a cofactor in the molecule and ferredoxin containing non-heme iron as a cofactor in the molecule transfer electrons from NADPH to P450.

The present inventors have already succeeded in industrially useful hydroxylations by producing several microsomal P450s and reductases in yeast and using their recombinant yeast strains.

That is, yeast strains producing the enzymes have been obtained by isolating genes for rat liver P450c, bovine adrenal $P450_{17}\alpha$ and $P450_{c21}$, respectively, making expression plasmids containing these genes, respectively, and transforming yeast with the expression plasmids (Japanese Patent Kokai (Laid-Open) Nos. 56072/1986, 47380/1989 and 31680/1990).

These yeast strains exhibited monooxygenase activities depending on P450 molecular forms produced therein, respectively.

The present inventors have also succeeded in the expression of the enzyme having P450 reducing ability within yeast by isolating rat liver reductase gene or yeast reductase gene (Japanese Patent Kokai (Laid-Open) Nos. 19085/1987 and 51525/1990).

Moreover, the present inventors have succeeded in creating a yeast strain which produces both P450 and reductase (Japanese Patent Kokai (Laid-Open) No. 104582/1987) and novel monooxygenases having the functions of both enzymes (Japanese Patent Kokai (Laid-Open) Nos. 44888/1988 and 23870/1990, and Japanese patent Application No. 71250/1989).

By these techniques, the present inventors have successfully produced acetaminophene or steroid hormone intermediates useful as medicines with these P450-producing yeast strains.

On the other hand, the mitochondrial P450 participates in many biological reactions which synthesize physiologically important compounds such as active vitamin $D_3$ and steroid hormones, and thus the creation of a yeast strain producing the mitochondrial P450 molecular form has a high industrial applicability.

However, there has not hitherto been reported the expression of an active mitochondrial P450 in yeast.

Furthermore, two enzymes, ferredoxin and ferredoxin reductase, are required in addition of P450 for the expression of mitochondorial P450-dependent monooxygenase activity.

Thus, the present inventors have tried to create a bioreactor for the expression of the mitochondorial P450 in yeast and of the mitochondrial P450-dependent monooxygenase activity.

Rat liver $P450_{c25}$ which is a mitochondrial P450 is synthesized as a precursor comprising 533 amino acids in cytoplasm and then transported to mitochondria. During these processes, 32 amino acids at the amino terminus acting as a mitochondrial targeting signal are removed to yield a matured $P450_{c25}$ comprising 501 amino acids (molecular weight: 57 KD) on the mitochondrial membrane.

The present inventors have already found that when a bovine adrenal mitochondrial protein is expressed in yeast, the substitution of its signal peptide part by that of yeast cytochrome c oxidase subunit IV (referred to hereinafter as COXIV) increases the expression amount remarkably (Japanese Patent Application No. 136496/1990).

SUMMARY OF THE INVENTION

Rat liver $P450_{c25}$ gene or a gene encoding the chimeric P450 (COX-C25) in which its own signal sequence had been substituted by the COXIV signal sequence was linked to the downstream of the promoter of a yeast alcohol dehydrogenase (ADH) gene for construction of expression plasmids. As a result, yeast strains transformed with these expression plasmids produced P450s containing heme.

It was also found that the $P450_{c25}$ and the chimetic P450 (COX-C25) thus produced were transported to the mitochondria in yeast and processed into the matured forms. Furthermore, the $P450_{c25}$ and the chimeric P450 (cox-c25) partially purified from these transformed yeast strains successfully produced TeHC or 1α, 25-dihydroxyvitamin $D_3$ from THC or 1α-hydroxyvitamin $D_3$ by coupling with bovine adrenal adrenodoxin (referred to hereinafter as ADX) and bovine adrenal NADPH-adrenodoxin reductase (referred to hereinafter as ADR).

Furthermore, the present inventors have constructed a plasmid for expressing the chimeric P450 (17α-c25) in which the mitochondrial targeting signal substituted by the N-terminal 15 amino acids derived from bovine adrenal P450$_{17α}$, which is believed to be a microsomal targeting signal of P450$_{17α}$ order to enhance the production of the enzyme inherently existing in mitochondria by exchanging its localization into microsomes.

The present inventors have also constructed a plasmid which express simultaneously the chimeric P450 (17α-c25), the matured ADX and the matured ADR for the purpose of constructing a novel electron transport chain with the chimeric P450 (17α-c25) on microsomal membrane and ADX and ADR in cytoplasm and exhibiting the monooxygenase activity. In this connection, these three enzymes were expressed with different promoters and terminators, because the use of the same promoter and the same terminator would cause recombination in the plasmid during the cultivation of the recombinant yeast.

It was found that all of the P450$_{c25}$, the chimeric P450 (COX-c25) and the chimeric P450 (17α-c25) expressed in yeast in the present invention exhibited hydroxylation activities to THC, vitamin D$_3$ and 1α-hydroxyvitamin D$_3$ and thus were active forms. Thus, the yeast expression system is useful for expressing the mitochondrial P450.

Particularly, the chimeric P450 (17α-c25) produces a large amount of the enzyme and has a high activity.

While P450$_{c25}$ and the chimeric P450 (COX-c25) were expressed in mitochondria in yeast, any chimetic P450 (17α-c25) expressed existed in microsomal fraction. Thus, the N-terminal 15 amino acid residues derived from P450$_{17α}$ played a role of a targeting signal of the chimeric P450 (17α-c25) to microsomal membrane in yeast, and the P450$_{c25}$ which is inherently mitochondrial membrane protein was successfully expressed in yeast microsome.

The production amount of the chimetic P450 (17α-c25) was about $2 \times 10^5$ molecules/cell, and thus the substitution of the signal successfully increased the production amount to about 4 times. Moreover, the microsomal fraction exhibited high hydroxylation activities to THC, vitamin D$_3$ and 1α-hydroxyvitamin D$_3$ by adding ADX and ADR to the fraction.

Particularly, the hydroxylation-activity to 1α-hydroxyvitamin D$_3$ of the chimeric P450(17α-c25) in the microsomal fraction was by far higher than that of the original matured P450$_{c25}$ comprising 501 amino acids in the mitochondrial fraction.

The present inventors has also succeeded in construction of a novel electron transport chain from NADPH to the chimeric P450 (17α-c25) through ADX and ADR on yeast microsomal membrane, as the simultaneous expression strain of chimetic P450 (17α-c25), ADX and ADR exhibits monooxygenase activity.

Therefore, the strain can be used as a simple bioreactor in which the hydroxylation of steroid compounds or an active vitamin D$_3$ is performed in one step.

Particularly, the strain can easily recover reaction products by adding a substrate to the culture of the microorganism and extracting with an organic solvent or the like after a certain period of time, so that it is useful as a bioreactor.

DETAILED DESCRIPTION OF THE INVENTION

The present invention will be explained in detail below.

cDNA encoding the rat liver P450$_{c25}$ used in the present invention is well known and can be isolated by the conventional procedures. The signal sequence portion to mitochondria can be substituted by a signal sequence of the other mitochondrial protein such as COXIV or the like. In this case, P450 is transported into mitochondria. On the other hand, if this signal sequence is substituted by a signal sequence to microsome, P450 is transported into microsome. As the transfer signal to microsome, not only bovine adrenal P450$_{17α}$ but also a transfer signal of the other microsmal P450 can be used.

Furthermore, as the matured mitochondrial P450 existing at the C-terminus of the chimeric P450 of the present invention, not only the rat liver P450$_{c25}$ but also the other mitochondrial P450 can be used.

cDNA encoding COXIV and bovine adrenal P450$_{17α}$ used in the present invention is well known and can be isolated by the conventional procedures.

For example, the expression plasmid for expressing the chimeric P450 (17α-c25) can be constructed by synthesizing cDNA corresponding the N-terminal amino acid sequence of bovine adrenal P450$_{17α}$, linking to the cDNA region encoding the matured rat liver P450$_{c25}$, and inserting the gene into the yeast expression vector pAAH5 which retains the promoter and the terminator of the yeast alcohol dehydrogenase I (referred to hereinafter as ADH) gene (Methods in Enzymology, 101, part C, 192–201).

The plasmid for simultaneously expressing the three enzymes can be constructed by inserting the expression units of the matured ADR and the matured ADX into he expression plasmid for the chimeric P450 (17α-c25). In this connection, the promoter and the terminator are not limited to ADH and may be the promoters and the terminators which function efficiently in yeast. The promoter and the terminator for expressing simultaneously the three enzymes are not the same and preferably different from each other, because recombination on plasmid will occur only with a low probability upon cultivation. The expression amount of the enzyme is scarcely affected by the position or the direction of the three enzymes to be inserted into the expression unit.

Yeast is used as a host, and the yeast *Saccharomyces cerevisiae* strain AH22 is preferred.

Transformation of yeast as a host by the expression plasmid can be conducted by the well-known methods such as that with an alkali metal (LiCl) or protoplast. Transformed yeast obtained by the present invention can be cultivated in an ordinary culture medium containing glucose, nitrogen sources or the like by the conventional methods. $P450_{c25}$ and the chimetic P450 can be produced by cultivating the transformed yeast strain thus obtained.

The present invention is described in detail with reference to Examples. However, it goes without saying that the present invention is not limited to Examples.

EXAMPLE 1

Construction of Expression Plasmid pAC25

Figure 1A:
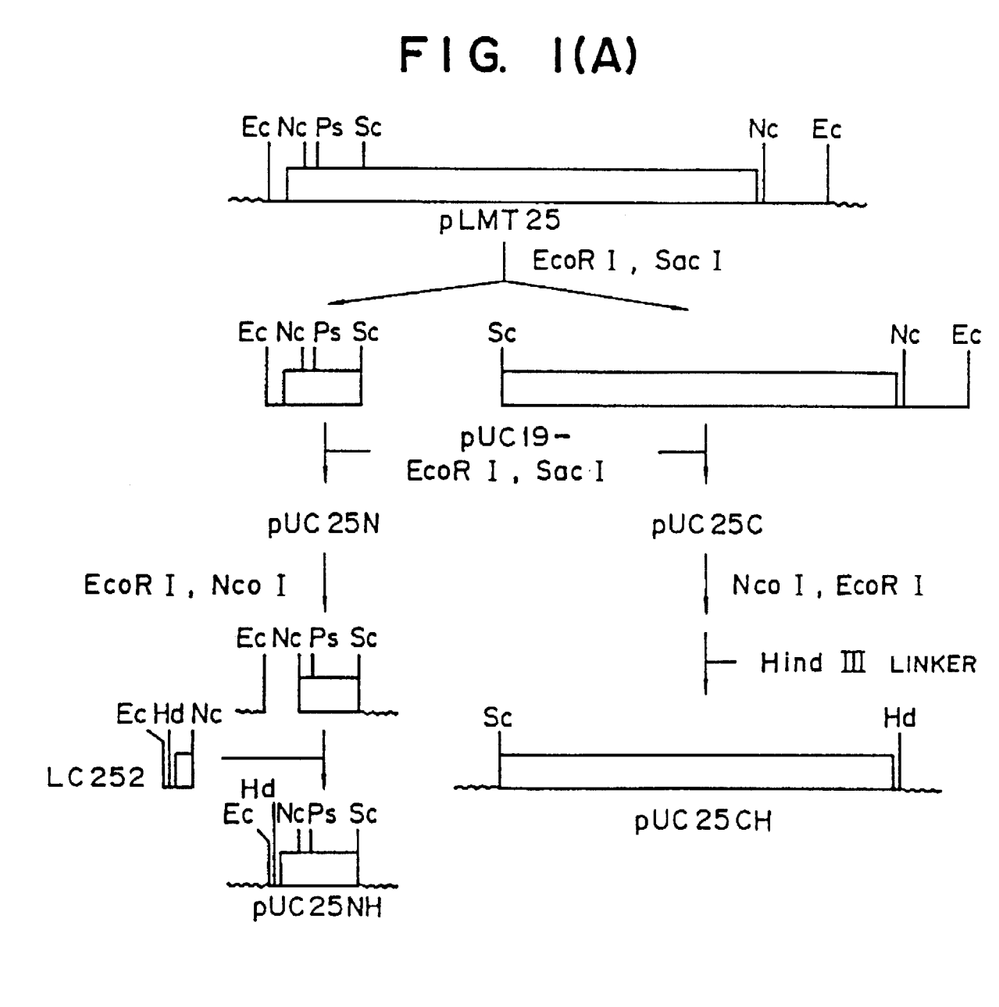
FIGS. 1A–B show the constructing process of the expression plasmid pAC25 of the present invention.
Figure 1B:
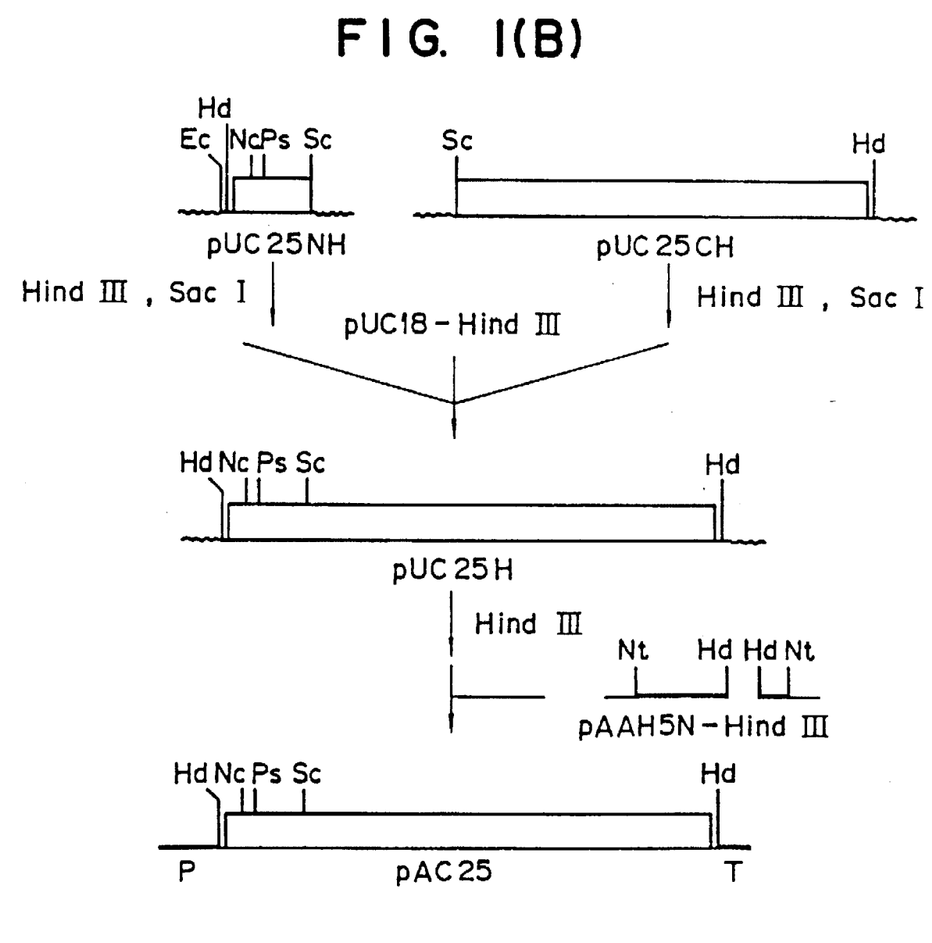

In the following Examples, the reactions such as the cutting of DNA with restriction enzymes, the dephosphorylation of DNA with alkaline phosphatase, the ligation of DNAs with DNA ligase were conducted generally with a reaction volume of 20≧200 μl Under the reaction conditions described in the instructions appended in the products of the manufacturers (e.g. Takara Shuzo Co., Ltd.) of these enzymes, unless otherwise specified. Rat liver $P450_{c25}$ expression plasmid was constructed in such a procedure as shown in FIG. 1.

Plasmid pLMT25 containing rat liver $P450_{c25}$ gene (Usui et al., (1990) FEBS Lett., 262, 135–138) was doubly digested with restriction enzymes EcoRI and SacI, and the ca. 320 bp EcoRI-SacI fragment encoding the region of the amino terminal side of $P450_{c25}$ and the ca. 1580 bp SacI-EcoRI fragment encoding the region of the carboxy terminal side were recovered by the low melting agarose gel electrophoresis. These fragments were subcloned at the EcoRI and SacI sites of a commercially available vector plasmid pUC19 to give pUC25N and pUC25C, respectively. A fragment of about 2880 bp obtained by the doubly digestion of pUC25N with EcoRI and NcoI, and a synthetic linker LC252:

analyzed by the digestion with restriction enzymes to obtain the aimed plasmid in which the synthetic linker was inserted. Further, the sequence of the synthetic linker part was confirmed by the determination of the base sequence. Thus, the plasmid obtained was named pUC25NH.

The plasmid pUC25C encoding the region of the carboxy terminal side of $P450_{c25}$ was digested with NcoI and fill-in ligated with a commercially available HindIII linker to transform E. coli strain HB101. Plasmid DNA was prepared from the transformant, and the plasmid in which a HindIII site was created in the 3'-non-coding region of $P450_{c25}$ was named pUC25CH.

Figure 2:
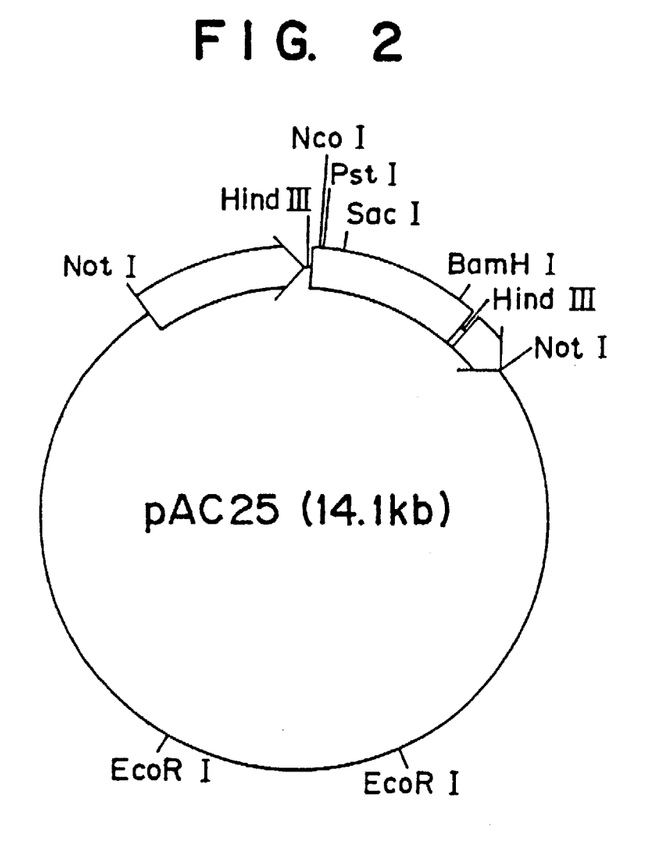
FIG. 2 shows a map of pAC25.

The fragments of about 270 bp and 1370 bp obtained by the doubly digestion of pUC25NH and pUC25CH with HindIII and SecI, respectively, and a commercially available vector plasmid pUC18 which had been digested with HindIII and treated with alkaline phosphatase were ligated to transform E. coli strain HB101. A plasmid DNA was prepared from the transformant, and the plasmid containing both DNA fragments derived from pU25NH and pUC25CH, respectively, was named pUC25H. pUC25H was digested with Hind III, and a cDNA fragment of ca. 1640 bp encoding the rat liver $P450_{c25}$ precursor was prepared. After the fragment and the yeast expression vector pAAH5N which had been digested with HindIII and then treated with alkaline phosphatase (Japanese Patent Application No. 202785/1988) were ligated, E. coli strain HB101 was transformed. A plasmid DNA was prepared from the transformant, the DNA structure was confirmed by restriction enzyme digestion and the plasmid in which the rat liver $P450_{c25}$ gene had been inserted in the right orientation between the ADH promoter and the terminator was named pAC25.

EXAMPLE 2

Construction of Expression Plasmid pACC253

Figure 3:
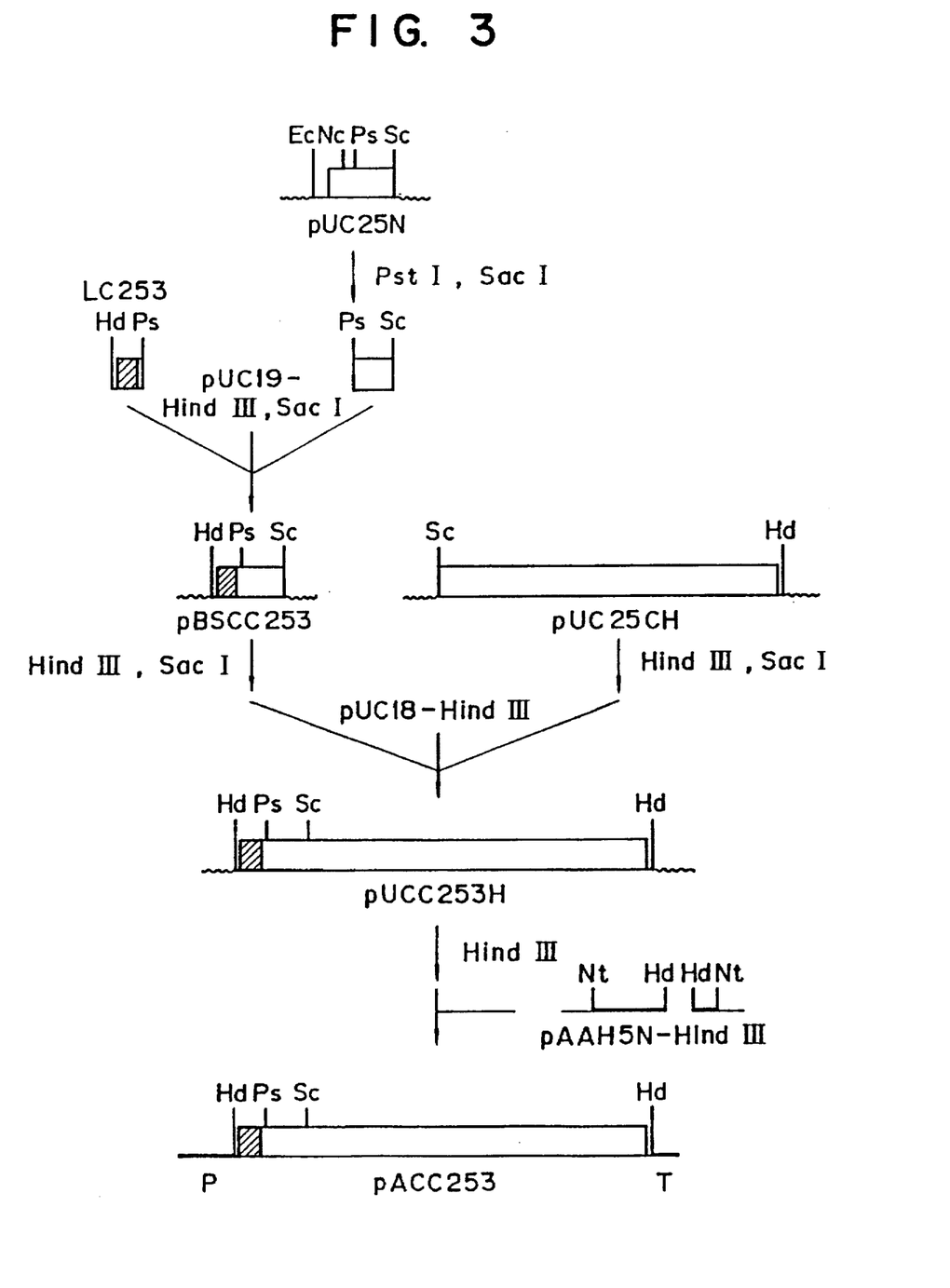
FIG. 3 shows the constructing process of the expression plasmid pAC253 of the present invention, in which the restriction enzyme sites represent the followings: Ec: EcoRI, Nc: NcoI, Sc: SacI, Hd: HindIII, Nt: NotI, Ps: PstI, and in the drawing, □ represents rat liver P450$_{c25}$ coding region, ■ represents yeast cytochrome c oxidase subunit IV coding region, and P and T represent ADH promoter and terminator, respectively.

Reference is made to FIG. 3.

Plasmid pUC25N containing the gene encoding the region of the amino terminal side of the rat liver $P450_{c25}$ was doubly digested with PstI and SacI to recover a fragment of about 150 bp. The fragment, the synthetic linker LC253:

(SEQ ID NO: 3)
5'AGCTTAAAAAAATGCTTTCACTACGTCAATCGATAAGATTTTTCAAGCCAGCCACAAGAAC (SEQ ID NO: 4)
3'ATTTTTTTACGAAAGTGATGCAGTTAGCTATTCTAAAAAGTTCGGTCGGTGTTCTTG

TTTGTGTAGCTCTAGATATCTGCTTCAGCAAAAACCCGCGATCCCTGCA 3'

AAACACATCGAGATCTATAGACGAAGTCGTTTTTGGGCGCTAGGG 5'

(SEQ. ID NO.1) 5'AATTCAAGCTTAAAAAAATGGCTCTGT-
TGAGCCGCATGAGA (SEQ. ID NO.2) 3'GTTCGAATTTTTTTACCGACACAACTCG-
GCGTACTCT

CTGAGATGGGCGCTTCTGGACACTCGTGTGATGGGC 3'

GACTCTACCCGCGAAGACCTGTGAGCACACTACCCGGTAC
5' which has EcoRI and NcoI recognition sites at right and left ends, respectively, and HindIII recognition site between the both ends, were ligated for transform E. coli strain HB101.

Plasmid DNA was prepared from the transformant thus obtained according to the Birnboim-Doly's method and which has HindIII and PstI recognition sites at right and left ends, respectively, and the HindIII-SacI fragment of a commercially available vector pUC19 were ligated, and E. coli strain HB101 was transformed. Plasmid DNA was prepared from the transformant thus obtained and analyzed by the digestion with restriction enzymes to obtain the aimed plasmid in which the fragment and the synthetic linker were inserted. Further, the sequence of the synthetic linker part was confirmed by the determination of the base sequence. Thus, the plasmid obtained was named pBSCC253. The plasmid and the aforementioned plasmid pUC25CH were doubly digested with HindIII and SacI, and a DNA fragment (ca. 260 bp) coding for the signal peptide of COXIV and the amino terminal part of $P450_{c25}$ and a DNA fragment (ca.

Figure 4:
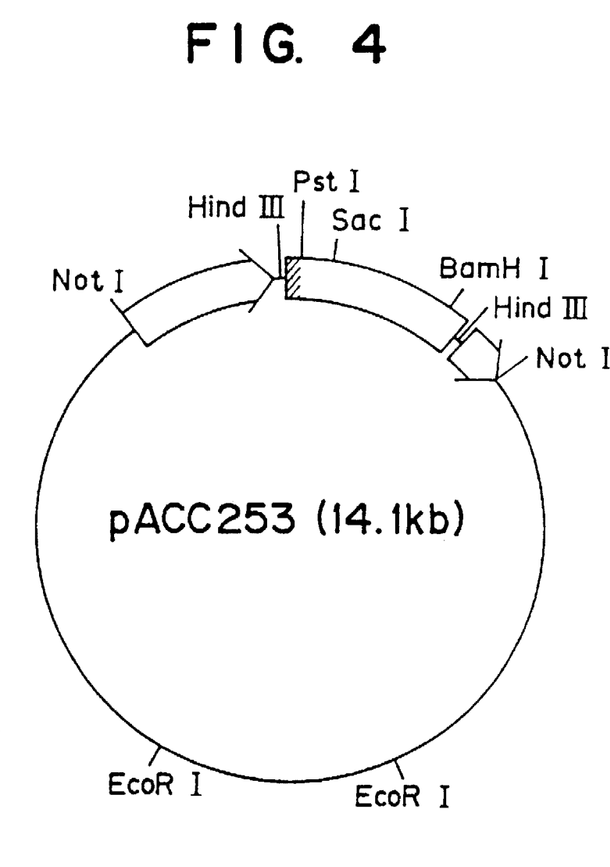
FIG. 4 is a map of PACC253.

1370 bp) coding for the carboxy terminal part of P450$_{c25}$ were recovered separately. The triple ligation of these fragments and a commercially available vector plasmid pUC18-HindIII fragment was conducted to transform *E. coli* strain HB101. A plasmid DNA was prepared from the transformant and analyzed by the digestion with restriction enzymes to obtain a plasmid pUCC253H in which the fragments had been inserted. pUCC253H was digested with HindIII to prepare a modified cDNA fragment (ca.1630 bp) for the rat liver P450$_{c25}$, which was ligated with the yeast expression vector pAAH5N which had been digested with HindIII and then treated with alkaline phosphatase (Japanese Patent Application No. 202785/1988), and then *E. coli* strain HB 101 was transformed. The structure of the plasmid DNA prepared from the transformant was confirmed, and the plasmid in which the rat liver P450$_{c25}$ modified gene had been inserted in the right orientation between the ADH promoter and the terminator was named pACC253.

EXAMPLE 3

Construction of Expression Plasmid pAMS25 and Simultaneous Expression Plasmid pRXMS25

Figure 5:
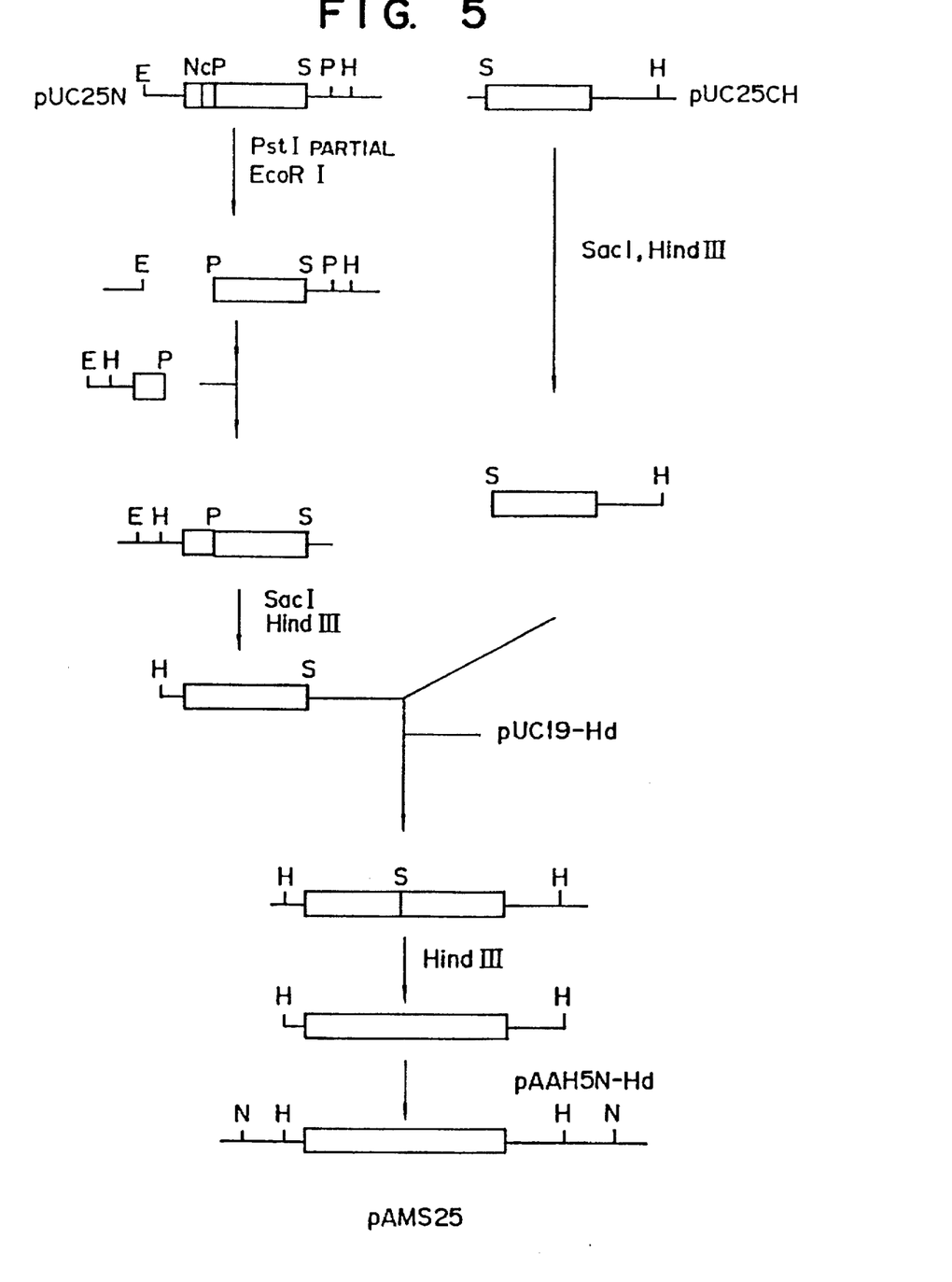
FIG. 5 is the explanatory drawing of the constructing process of the expression plasmid of the present invention pAMS25, in which the restriction enzyme cutting sites are represented as follows: E: EcoRI, Nc: NcoI, S: SacI, H: HindIII, P: PstI, N: NotI.

The chimeric P450 (17α-c25) expression plasmid pAMS25 was constructed according to FIG. 5.

The plasmid pUC25N used in the rat liver P450$_{c25}$ expression plasmid pAC25 illustrated in Example 1 was partially digested with PstI and then with EcoRI. Into the DNA fragment obtained was inserted a synthetic linker: sequence (SEQ ID NO:5)

AATTCAAGCT TAAAAAAATG TGGCTGCTCC TGGCT-GTCTT TCTGCTCACC CTCGCCTATT60 GTTCGA ATT-TTTTAC ACCGACGAGG ACGACAGAA AGACGAGTGG GAGCGGATAA TAGCGATCCC TGCA 74 ATCGCTAGGG and a HindIII-SacI fragment was prepared from the plasmid thus obtained. Also, a SacI-HindIII fragment was prepared from pUC25CH and doubly inserted into the HindIII site of pUC19 for obtaining a plasmid pUMS25.

Next, an expression plasmid pAMS25 was constructed by inserting the HindIII fragment obtained from pUMS25 into the Hind III site of a vector pAAH5N.

Figure 6:
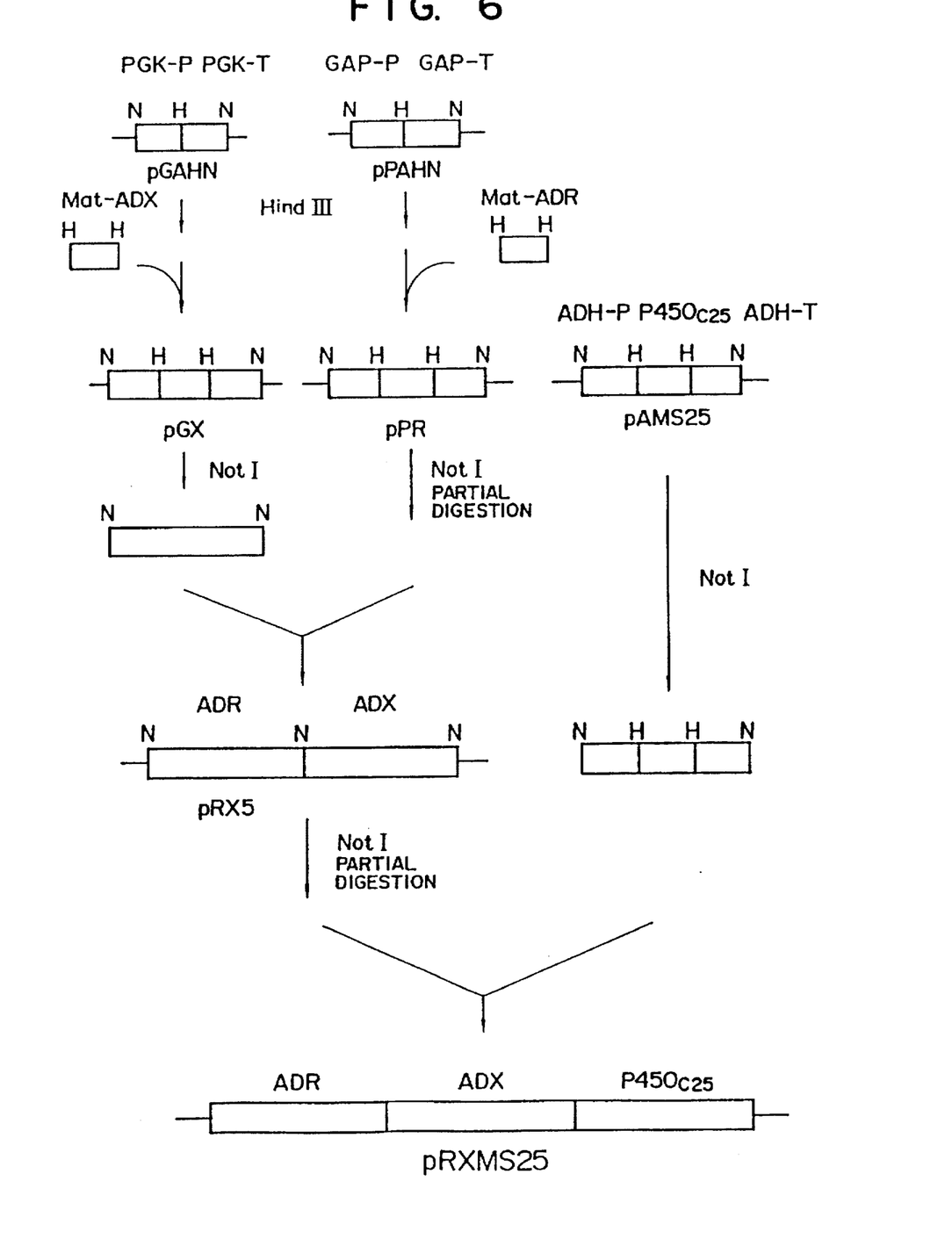
FIG. 6 is the explanatory drawing of the constructing process of the expression plasmid of the present invention pRXMS25, in which the restriction enzyme cutting sites are represented as follows: H: HindIII and N: NotI.

An expression plasmid pGX was obtained by inserting a Hind III fragment coding for the matured ADX (described in Japanese Patent Application No. 136496/1990) between the PGK promoter and the terminator of a vector pGAHN (containing the PGK promoter and the terminator in place of the ADH promoter and the terminator of a vector pAAH5N) (described in Japanese Patent Application No. 136496/1990). pPR was also prepared by inserting a Hind III fragment coding for the matured ADR (described in Japanese Patent Kokai No. 112986/1988) between the GAP promoter and the terminator of a vector pPAHN, which contains the GAP promoter and the terminator (Japanese Patent Kokai (Laid-Open) No. 112986/1988) in place of the ADH promoter and the terminator of the vector pAAH5N). Simultaneous expression plasmid pRX5 for ADR and ADX was obtained by ligating the DNA fragment obtained by partially digesting pPR with NotI and the NotI fragment obtained from pGX. Then, pRX5 was partially digested with NotI, ligated with a NotI fragment (3.7 kb) obtained from pAMS25 to obtain the simultaneous expression plasmid pRXMS25 for the chimeric P450$_{c25}$, ADX and ADR (See FIG. 6).

EXAMPLE 4

Transformation of Yeast with Expression Plasmid

*Saccharomyces cerevisiae* AH22 (ATCC 38626) was cultivated in 5 ml of a YPD culture medium (1% yeast extract, 2% polypeptone, 2% glucose) at 30° C. for 18 hours, and the yeast cells were collected by centrifuging 1 ml of the culture. The yeast cells were washed with 1 ml of a 0.2M LiCl solution and then suspended into 20 µl of a 1M LiCl solution.

To this suspension were added 30 µl of a 70% polyethylene glycol 4000 solution and 10 µl of respective expression plasmid solutions (about 1 µg DNA), and the mixture was stirred well and incubated at 30° C. for 1 hour. Then, 140 µl of water was added to the mixture, and the resulting mixture was inoculated on an SD synthetic culture medium plate (2% glucose, 0.67% yeast nitrogen base without no amino acids, 20 µg/ml histidine, 2% agar) and incubated at 30° C. for 3 days to give a transformant in which the plasmid was maintained.

EXAMPLE 5

Production of P450$_{c25}$ and Chimera P450$_{c25}$

The strains AH22/pAC25, AH22/pACC253, AH22/pAMS25 and AH22/pRXMS25 obtained in Example 4 were cultivated in 300 ml of a synthetic culture medium (8% glucose, 5.4% yeast nitrogen base without amino acids, 160 µg/ml histidine) to a density about 2×10$^7$ cells/ml, and the recombinant yeast cells were collected, washed with 100 mM potassium phosphate (pH 7.0) and suspended into 2 ml of the same buffer solution. A 1 ml portion of the suspension was dispensed into each of the two cuvettes, carbon monoxide was blown into the sample cuvette, and then 5–10 mg of dithionite was added to both of the cuvettes. After sufficiently stirring the mixtures, the differential spectra were measured in the wave length of 400–500 nm to calculate the amount of the heme-containing P450 based on Δε (450 nm–490 nm)=91 mM$^{-1}$·cm$^{-1}$.

As the result, it was found that the strains AH22/pAC25, AH22/pACC253, AH22/pAMS25 and AH22/pRXMS25 produced a heme-containing P450 in an amount of 5×10$^4$ molecules, 3×10$^4$ molecules, 2×10$^5$ molecules and 1×10$^5$ molecules per cell, respectively. On the other hand, no production of the heme-containing P450 was observed in the control strain AH22/pAAH5.

EXAMPLE 6

Measurement of the Hydroxylation Activity at 25 Position of 1α-hydroxy-vitamin D$_3$ and the Hydroxylation Activity at 27 Position of THC A mitochondrial fraction prepared from the strain AH22/pAC25 and a microsomal fraction prepared from the strain AH22/pAMS25 were used for the measurement of hydroxylation activities. Subcellular fractionation was prepared from a transformant yeast strain according to the following method. About 4×10$^{10}$ cells were collected from a culture containing about 2×10$^7$ cells/ml, suspended in Zymolyase solution [10 mM Tris-HCl (pH 7.5), 2.0M sorbitol, 0.1 mM dithiothreitol, 0.1 mM EDTA, 0.3 mg/ml Zymolyase 100T] and incubated at 30° C. for 1 hour to prepare spheroplasts. The spheroplasts were suspended in a sonication buffer (10 mM Tris-HCl (pH 7.5), 0.65M sorbitol, 0.1 mM dithiothreitol, 0.1 mM EDTA, 1 µg/ml leupeptin, 1 µg/ml pepstatin) and homogenized with a Teflon homogenizer to disrupt the cells.

Precipitate 1 was removed by centrifugation at 3000×g for 5 minutes to give supernatant 1'. Precipitate 1 was resuspended in a sonication buffer, homogenized again, centrifuged at 3000×g for 5 minutes to give precipitate 1

(undisrupted cells and nucleus fractions) and supernatant 1". Supernatant 1 comprising supernatant 1' and supernatant 1"was further centrifuged at 10,000×g for 20 minutes to give precipitate 2 (mitochondrial fraction) and supernatant 2. Supernatant 2 was further centrifuged at 120,000×g for 70 minutes to give precipitate 3 (microsomal fraction) and supernatant 3 (soluble fraction).

Reaction systems (2 ml) shown in the following but NADPH were mixed and preincubated at 37° C. for 5 minutes, and reaction was initiated by the addition of NADPH. After 5 and 10 minutes, 0.5 ml portions of reaction solutions were taken, respectively, and 5 ml of benzene was added to the removed samples. The benzene layer obtained by centrifugation was dried completely and analyzed by HPLC under the condition listed below.

[Reaction System]

| | |
|---|---|
| 1. Mitochondrial fraction: strain AH22/pAC25 (containing 0.1 nmol $P450_{c25}$), Microsomal fraction: strain AH22/pAMS25 (containing 0.8 nmol chimeric P450 (17α-c25)), | |
| 2. Bovine adrenal adrenodoxin reductase | 0.8 nmol, |
| 3. Bovine adrenal adrenodoxin | 8.0 nmol, |
| 4. Substrate final concentration | 200 µM, |
| 5. NADPH final concentration | 1.0–2.0 mM, |
| 6. Tris-HCl (pH 7.8) | 100.0 mM, |
| 7. EDTA | 0.5–1.0 mM. |

[HPLC Analysis Condition]

Column: µBondapak C18 (φ4×300 mm).

Detection: A265 (1α-hydroxyvitamin D3), Radioactive detector ($^3$H-THC),

Flow rate: 1.0 ml/min,

Temperature: 50° C.,

Elution condition

0–5 min: 80% acetonitrile–20% water solution

5–15 min: linear concentration gradient of 80% –100% acetonitrile,

15–25 min: 100% acetonitrile

When 1α-hydroxyvitamin $D_3$ was used as a substrate, the 25-hydroxylated product were observed in the mitochondrial fraction of the strain AH22/pAC25 and the microsomal fraction of the strain AH22/pAMS25. On the other hand, no 25-hydroxylated products were observed in the control strain AH22/pAAH5. Thus, it was suggested that the hydroxylation activities are dependent on $P450_{c25}$ and the chimetic P450 (17α-c25).

In addition, no activity was detected in the absence of either NADPH, ADX or ADR, so that the hydroxylation activities were believed to be exhibited with the construction of the electron transfer chain, NADPH→ADR→$P450_{c25}$ or chimeric P450 (17α-c25), which was formed on the addition of NADPH, ADX and ADR.

In the microsomal fraction of the strain AH22/pAMS25, the calculated turnover number was 7.4 mol/mol P450/min, and thus it was found that the rate was about 50 times higher than the calculated turnover number obtained in the mitochondrial fraction of the strain AH22/pAC25 of 0.14 mol/mol P450/min. When [$^3$H]-THC was used as a substrate, the transformation of THC to the 27-hydroxylated product (TeHC) was observed in the mitochondrial fraction of the strain AH22/pAC25 and the microsomal fraction of the strain AH22/PAMS25. No activity was observed in the control strain AH22/pAAH5. Thus, it was suggested that the activity was dependent on $P450_{c25}$ and chimetic P450 (17α-c25). The turnover numbers calculated in the mitochondrial fraction of the strain AH22/pAC25 and the microsomal fraction of the strain AH22/pAMS25 were 20 mol/mol P450/min and 23 mol/mol P450/min, respectively.

EXAMPLE 7

Measurement of the 27-hydroxylation Activity of THC in the Triple Simultaneous Expression Strain AH22/pRXMS25

To the culture of the strain AH22/pRXMS25 (1.6×10$^7$ cells/ml) was added [$^3$H]-THC so that the final concentration is 10 µM, and the incubation was continued. A 1 ml portion of the culture after 14 hour cultivation was taken out and extracted with 2 ml of dichloromethane, and the dichloromethane layer was evaporated to dryness, dissolved in 80 µl of acetonitrile, of which a 50 µl portion was analyzed by HPLC under the same condition as described in Example 6. As a result, it was found that 19% of the substrate THC added had been transformed into TeHC. Such transformation was not observed in the control strain AH22/pAAH5, and thus it was found that the chimetic $P450_{c25}$, ADX and ADR constructed an electron transport chain and exhibited a monooxygenase activity in the strain AH22/pRXMS25.

The transformed yeast provided by the present invention produces $P450_{c25}$ containing heme in the molecule and the chimeric $P450_{c25}$.

$P450_{c25}$ and the chimeric $P450_{c25}$ exhibited 25-hydroxylation activities to vitamin $D_3$ and 1α-hydroxyvitamin $D_3$ and 27-hydroxylation activity to THC by the addition of bovine adrenal ADX and ADR.

While $P450_{c25}$ is a protein inherently present in mitochondrial inner membrane, conversion from mitochondria to microsome for its localization in yeast cells was succeeded by removing the mitochondrial targeting signal and adding the N-terminal 15 amino acid residues derived from the microsomal $P450_{17α}$, which functions as a targeting signal to microsomal membrane. Such a conversion of the localization of the membrane enzyme has not hitherto been reported in the literatures. While the 15 amino acid residues at the N-terminus of $P450_{17α}$ are highly hydrophobic and is believed to play a role as a targeting signal to microsomal membrane, it has no specificity as a signal and can be replaced with a signal of the other microsomal membrane proteins.

The production amount of $P450_{c25}$ per yeast cell could be increased to about 4 times and the 25-hydroxylation activity of 1α-hydroxyvitamin $D_3$ per P450 molecule could be also increased to about 50 times by changing mitochondria into microsome for the localization of membrane enzyme based on the substitution of the signal. Thus, the ability of the 25-hydroxylation of 1α-hydroxyvitamin $D_3$ per cell was assumed to be raised to about 200 times. It is possible to produce 1α, 25-dihydroxyvitamin $D_3$ which plays a role for regulating calcium metabolism, stimulating the differentiation of cells and controlling cellular immune systems and is useful for the treatment of osteoporosis, chronic renal insufficiency, vitamin D resistant rickets or the like by using $P450_{c25}$ or the chimeric $P450_{c25}$ as a bioreactor.

In addition, the use of the cells of the strain which expresses simultaneously chimeric $P450_{c25}$, ADX and ADR as a bioreactor is a useful means for simplifying the currently used complex method for chemical synthesis of an active vitamin $D_3$.

Further, $P450_{c25}$ produced in yeast can be easily purified, and an antibody against $P450_{c25}$ can be used as a diagnostic agent of cerebrotendinous xanthomatosis. It has been definitely shown that the patients of cerebrotendinous xanthomatosis are congenitally defficient in the enzyme. The disease is characterized in xanthomatosis or the neuropathy of animus, and xanthomatosis is generated at Achilles tendon, lung and brain of the patient resulting in serious symptoms such as cataract, lowering of intelligence or the like. It is known that the cholestanol level in the serum of the patients is in a proportion of 10–100 to the normal level, and diagnostic methods utilizing this phenomenon or methods of measuring the activity of the enzyme with THC labelled with a radioisotope are currently used. The production of $P450_{c25}$ in a large scale has become possible by cultivating the strain of the transformed yeast obtained by the present invention, so that the preparation of an antibody against the isolated and purified enzyme makes it possible to detect $P450_{c25}$ at a high sensitivity and is believed to be effective for the diagnosis of cerebrotendinous xanthomatosis.

What we claimed is:

1. A yeast expression plasmid comprising DNA encoding a mitochondrial P450 which is a chimeric cytochrome $P450_{17\alpha\text{-}c25}$ which consists of $P450_{c25}$ having its targeting signal substituted by DNA encoding the N-terminal 15 amino acids of bovine adrenal cytochrome $P450_{17\alpha}$, operably linked to a promoter and terminator that is operative in yeast.

2. The yeast expression plasmid according to claim 1, wherein said promoter and terminator are the yeast alcohol dehydrogenase promoter and terminator.

3. The yeast expression plasmid according to claim 1, which further comprises DNA encoding the mature form of bovine adrenal adrenodoxin and DNA encoding the mature form of bovine adrenal NADPH-adrenodoxin reductase.

4. The yeast expression plasmid according to claim 3, wherein said promoter and terminator are the yeast alcohol dehydrogenase promoter and terminator, and said DNA encoding the mature form of bovine adrenal adrenodoxin is operatively linked between a phosphoglycerate kinase promoter and terminator and said DNA encoding the mature form of bovine adrenal NADPH-adrenodoxin reductase is operatively linked between a glyceraldehyde-[e]3-phosphate dehydrogenase promoter and terminator.

5. The yeast expression plasmid pAMS25.

6. The yeast expression plasmid pRXMS25.

7. Yeast containing the yeast expression plasmid of claim 1.

8. A yeast containing the yeast expression plasmid of claim 2.

9. A yeast containing the yeast expression plasmid of claim 4.

10. A yeast containing the yeast expression plasmid of claim 5.

11. A yeast containing the yeast expression plasmid of claim 6.

12. A process for producing a chimeric cytochrome P450 17α-25 which comprises cultivating a yeast strain containing the expression plasmid of claim 1.

13. A process for producing 5 β-cholestane-3α,7α,12α,27-tetrol, 25-hydroxyvitamin $D_3$ or 1α,25-dihydrovitamin $D_3$, which process comprises reacting 5-β-cholestane-3α,7α,12α-triol, vitamin $D_3$ or 25-hydroxyvitamin $D_3$ respectively with a culture of a yeast containing the expression plasmid of claim 1.

14. A process for making 5-β-cholestane-3α, 7α, 12α-27-tetrol, 25-hydroxyvitamin $D_3$ or 1α,25-dihydroxyvitamin $D_3$, which comprises contacting 5-β-cholestane-3α, 7α,12α-triol, vitamin $D_3$ or 25-hydroxy vitamin $D_3$, respectively, with a microsomal fraction obtained from a yeast of claim 1.

\* \* \* \* \*